United States Patent [19]
Torii et al.

[11] Patent Number: 5,990,167
[45] Date of Patent: *Nov. 23, 1999

[54] ACTIVITY-INHIBITOR AND ACTIVITY-POTENTIATOR FOR GLUTAMIC ACID IN THE BRAIN

[75] Inventors: Kunio Torii, Tokyo; Takashi Kondo, Toyama, both of Japan; Hrudananda Mallick, New Delhi, India

[73] Assignees: Japan Science and Technology Corporation, Saitama; Ajinomoto Co., Inc., Tokyo, both of Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/909,492

[22] Filed: Aug. 12, 1997

[30] Foreign Application Priority Data

Aug. 12, 1996 [JP] Japan .................................. 8-212838

[51] Int. Cl.$^6$ .................................................. A61K 31/195
[52] U.S. Cl. ............................................................ 514/564
[58] Field of Search ...................................... 514/561, 564

[56] References Cited

U.S. PATENT DOCUMENTS

| | | | |
|---|---|---|---|
| 4,372,774 | 2/1983 | Fish et al. ................................ | 424/319 |
| 5,373,085 | 12/1994 | Fox et al. ................................ | 528/328 |
| 5,470,846 | 11/1995 | Sandyk .................................... | 514/159 |
| 5,587,399 | 12/1996 | Acousta et al. ......................... | 514/561 |
| 5,602,150 | 2/1997 | Lidsky .................................... | 514/327 |
| 5,643,954 | 7/1997 | Komissarova et al. ................. | 514/561 |
| 5,668,117 | 9/1997 | Shapiro .................................... | 514/55 |
| 5,691,325 | 11/1997 | Sandyk .................................... | 514/159 |
| 5,693,614 | 12/1997 | Torii et al. ............................... | 514/12 |
| 5,731,349 | 3/1998 | Komissarova et al. ................. | 514/561 |

OTHER PUBLICATIONS

Chang et al II Eur. J. Pharmacol 233 12–3 209–217, p. 66, 36–37, (1993).
Chang et al. III Neurochem. Res. 20(8):931–937, p. 61–62, (1995).
Chang et al I Eur. J. Pharmacol. 193(2) 239–247, p. 68–69, (1991).
Starr et al Pharmacol Biochem Behav 4512:321–325, p. 34–35, (1993).
Pautler Medical Hypothesis 42(6):363–366, p. 72–73, (1994).
Dorheim et al Biochemical Biophys Res. Commun. 205/1:659–665, p. 29–30, (1994).
Rigaud–Monnet et al Brain Research 673/2:297–303, p. 25–25, (1995).
Herberg et al. Psycho Pharmacology 119(1):115–123, p. 64–65 22–23, (1995).
Habu et al Biochem Mol. Biol. Int. 39(1):87–95, p. 59–60, (1996).
Prendergast et al Pharmacol Biochem Behav. 56(1):81–87, p. 60, (1997).

*Primary Examiner*—James H. Reamer
*Attorney, Agent, or Firm*—Fish & Richardson P.C.

[57] ABSTRACT

The present invention provides an activity-inhibitor for glutamic acid in the brain which comprises L-lysine or its derivatives. The present invention also provides an activity-inhibitor for glutamic acid in the brain which comprises L-arginine or its derivatives. The present invention further provides an activity-potentiator for glutamic acid in the brain which comprises glycine or its derivatives.

7 Claims, 3 Drawing Sheets

ACTIVITY-INHIBITOR AND ACTIVITY-POTENTIATOR FOR GLUTAMIC ACID IN THE BRAIN

FIELD OF THE INVENTION

The present invention relates to an activity-inhibitor and activity potentiator for glutamic acid that is a major excitatory neurotransmitter in the central nervous system. The drugs according to the present invention are effective for prevention or treatment of various diseases caused by an abnormal activity of glutamic acid in the brain such as dementia and epilepsy, respectively.

BACKGROUND OF THE INVENTION

The highly developed motor and mental function of human beings are controlled by a complicated communication network of a large number of nerve cells (neurons).

In this neural network, activity of each neuron (electrical signal) is transmitted to the target neurons through the neurotransmitter (chemical signal) released to the terminal junctions of the neuron (synaptic cleft). The neurotransmitter is stored within vesicles (synaptic vesicles) present at the nerve terminal and when a depolarization occurs due to an electrical activity of the neuron, the calcium channel at presynaptic membrane is opened and the neurotransmitter is then released by an influx of extracellular calcium ion into the nerve terminal. The neurotransmitter diffuses into the synaptic cleft, reaches the receptor at postsynaptic membrane of the target neuron, and then opens its sodium channel to cause new electrical activity. Since the type of neurotransmitter to be released has already been determined at each synapse and the affinity of each neurotransmitter for its receptor has also been determined, a specific information is transmitted through the intrinsic pathway in the network.

As a type of the neurotransmitters, a great variety of substances are known such as amines, amino acids and neuropeptides. Recently, it has been pointed out that glutamic acid, belonging to amino acid-type neurotransmitter, plays an important role in memory and motor function. For example, reduction of a long-term potentiation (phenomenon wherein an electrical response of neurons for a temporal electrical stimulation after tetanic stimulation is maintained for a long term) in hippocampus and impairments of spatial memory were observed in the mice that lacks ε1 subunit of the glutamic acid receptor (NMDA receptor), and it is therefore suggested that glutamic acid is involved in neural plasticity and memory formation. (Nature, Jan. 12, 1994, p.151). Additionally, in the mice in which metabolic glutamic acid receptor-1 (mGluR1) had been deleted, abnormal motor activity and impairment of spatial memory were also observed although there was little anatomical and electrophysiological difference between this deficit and normal mice (Nature, Nov. 17, 1994, p.237).

Furthermore, the following evidences are reported, which support the influences of glutamic acid in the brain on memory and motor function.

(1) A large number of neurons which uses glutamic acid as a neurotransmitter (glutamatergic neurons) are located in hippocampus and cerebellum that is closely involved in learning and memory.

(2) A modulation of transmission efficacy at the synapse, which would be involved in fundamental mechanism of learning and memory, is plastically occurred in a synapse wherein glutamic acid is used as a neurotransmitter. That is, it is known that phenomenon such as long-term potentiation or long-term depression is occurred in a postsynaptic membrane followed by a temporal modulation of an input induced by glutamic acid.

(3) Rats with bilateral lesions of hippocampus or with intraventricular administration of an antagonist for glutamic acid receptor (NMDA receptor) to inhibit an activity of the glutamic acid in the brain, can not learn the position of a platform in the water in the spatial learning of Morris's water maze task (Nature, Feb. 27, 1986, p.774).

Reviewing these evidences, it is considered that a reduction of glutamic acid activity in the brain causes an impairment of the transmission due to reduced excitation in neurons and then causes symptom of memory impairment such as dementia. Alternatively, it is also considered that, when an excess activity of glutamic acid influences motor neurons, it causes motor disturbances such as epilepsy. Accordingly, it is expected that these diseases can be prevented or improved by potentiating the reduced transmission or inhibiting the excess activity, respectively.

Accordingly, the object of the present invention is to provide the activity-potentiator and activity-inhibitor for the glutamic acid in the brain.

SUMMARY OF THE PRESENT INVENTION

The present invention provides an activity-inhibitor for glutamic acid in the brain, which comprises L-lysine or its derivatives as an effective component in order to solve the above problems.

The present invention also provides an activity-inhibitor for glutamic acid in the brain, which comprises L-arginine or its derivatives as an effective component.

The present invention further provides an activity-potentiator for glutamic acid in the brain, which comprises glycine or its derivatives as an effective component.

DETAILED DESCRIPTION OF THE INVENTION

Figure 1:
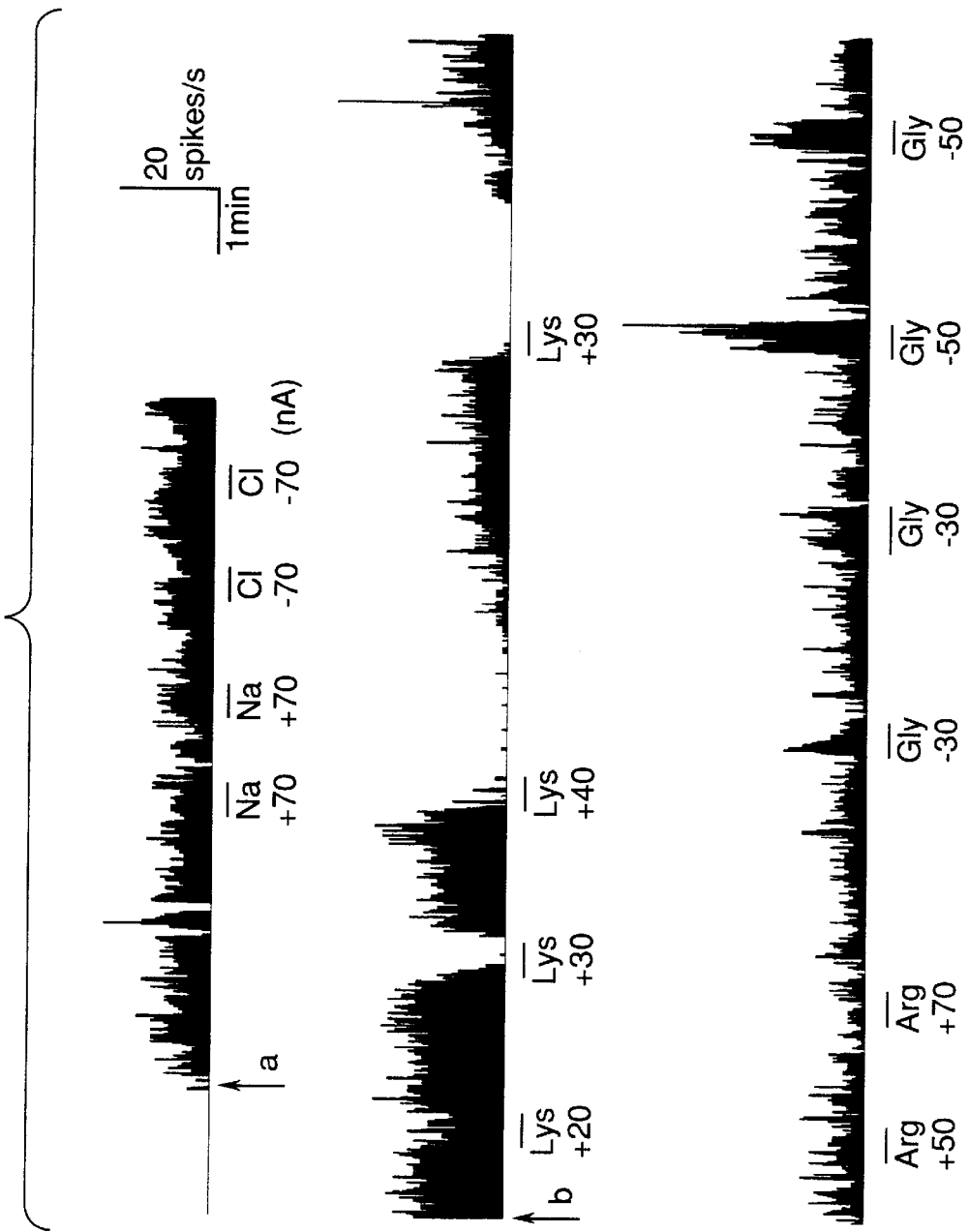
FIG. 1 shows an example of single neuronal activity, which shows influences of lysine (Lys), arginine (Arg) and glycine (Gly) on glutamic acid-induced neuronal activity in the ventromedial hypothalamus (VMH). Basal neuronal activity was evident by a continuous release of glutamic acid using an electrical current of 10 nA (a) and 20 nA (b).

In the present invention, "activity-inhibition of glutamic acid in the brain" means an inhibitory effect for an abnormal excitation of neurons caused by an excess glutamatergic neurotransmission. The drug having such an inhibitory effect may be effective for prevention or treatment of motor disturbances such as epilepsy.

"Activity-potentiation of glutamic acid in the brain" means a potentiating effect for a reduced glutamatergic neurotransmission. The drug having such a potentiating effect may be effective for prevention or treatment of memory disturbances such as dementia caused by impairment of transmission due to a reduced excitation of neurons.

The inventors of the present invention already filed a patent application claiming an anti-dementia drug comprising arginine as one of effective components (Japanese Patent Laid-Open Application Hei 3 (1991)-275631). However, the anti-dementia drug of this prior invention is used for relieving symptoms of dementia caused by ischemia in the brain. This drug provides resistance for nerve cells to neurotransmitters such as glutamic acid and aspartic acid in order to prevent necrosis of the nerve cells caused by the neurotransmitter excessively released as a result of metabolic abnormality in the brain after ischemia. Such substances providing a resistance may be actually acidic fibroblast growth factor (aFGF), and arginine is only disclosed as one example of substances which are able to promote the secretion of this aFGF. Accordingly, arginine used as an effective component in the present invention completely differs from one used in the above prior invention in the application purpose, and of course the present invention never denies the effectiveness of the prior invention.

The activity-inhibitor or activity-potentiator according to the present invention contains amino acids (lysine, arginine, and glycine) and its derivatives as an effective component and may be safely used as a medicine or a food additive. When used as a medicine, the present inhibitor or potentiator may be administered orally, intravenously, or eterally. It may be formed into a desired dosage form depending upon an administration pathway to be used. Although a dosage of the present inhibitor or potentiator may be varied according to the type and symptom of diseases, it may be administered to one adult in an amount of 1–100 g per day.

The amino acids mentioned above may include those which are synthesized in a known manner or those which are optionally prepared in a known manner, for example, resemblance having various protective groups for amino and carboxyl groups, their salts, or condensates.

The effectiveness of each amino acid used in the present invention will be further illustrated by the following biological tests using experimental animals (aroused rats).

EXAMPLES (1) Procedure

Extracellular single neuronal activity was recorded from the ventromedial hypothalamus (VMH) of aroused Wistar rats (male) in accordance with a published method (Nakamura, K. & Ono, T.; J. Neurophysiol., 55, p.163–181, 1986). In detail, single neuronal activity was recorded by using the eight-barreled glass-micropipette with a carbon fiber (7 $\mu$m diameter)-cored glass-microelectrode in its center which was protruded 15–20 $\mu$m from the tip of the center micropipette. Five barrels were filled with monosodium glutamate (0.05 M; pH 8.5), lysine HCl (0.05 M; pH 6.0), arginine (0.05 M; pH 6.0), glycine (0.05 M; pH 8.5) and NaCl (0.15 M), respectively, and each chemical substance was released iontophoretically from each barrel by applying a suitable polar electric current of 10–90 nA. Two barrels were filled with 4M NaCl in order to take balance of the electric current. Each chemical substance was administered for 30–60 seconds with an interval great enough interval so that the neurons can recover from the effects of the chemical substances. Furthermore, Na$^+$ and Cl$^-$ were released in order to evaluate the nonspecific current effect for the neurons.

A statistical significance was obtained when activity of the neuron was changed by more than 30% under the release of each chemical substance. A recorded site of the neurons was histologically confirmed.

(2) Results

Fifty single neuronal activities were recorded from the VMH. Twenty-five neurons showed spontaneous activity and the other 25 neurons showed a little or no spontaneous activity thereby glutamic acid was administered continuously to induce neuronal activity (glutamic acid-induced activity). Neurons with spontaneous activity were further excited by the administration of glutamic acid, but they did not responded by the administration of lysine, arginine or glycine.

Figure 2:
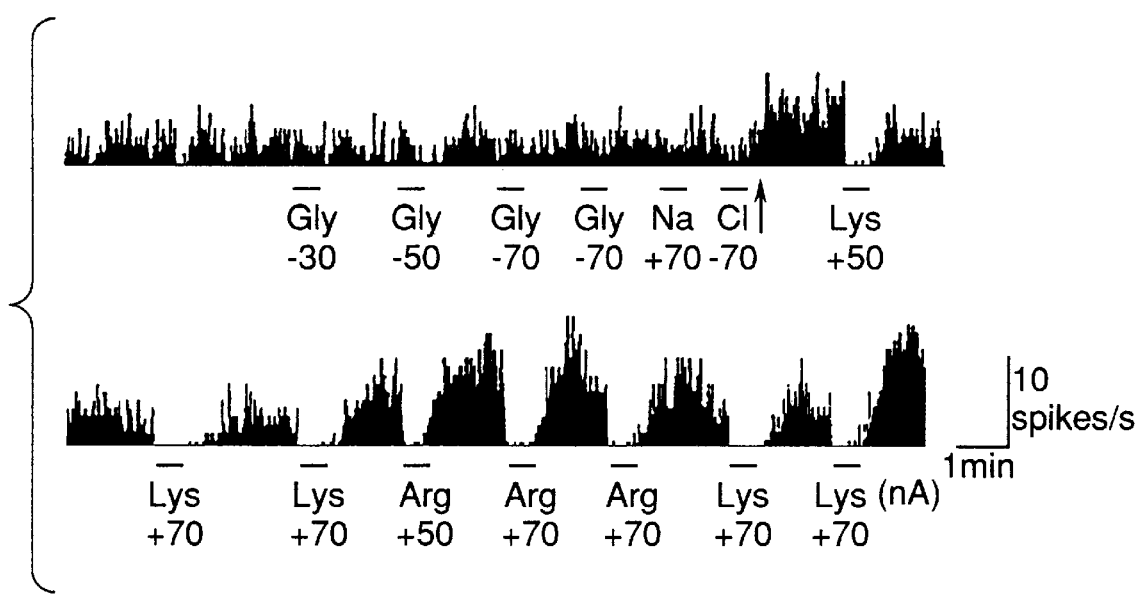
FIG. 2 shows an example of single neuronal activity, which shows influences of lysine (Lys), arginine (Arg) and glycine (Gly) on glutamic acid-induced neuronal activity in the VMH. Basal neuronal activity caused by a continuous release of glutamic acid using an electrical current of 10 nA (from the beginning) and 20 nA (after arrow).
Figure 3:
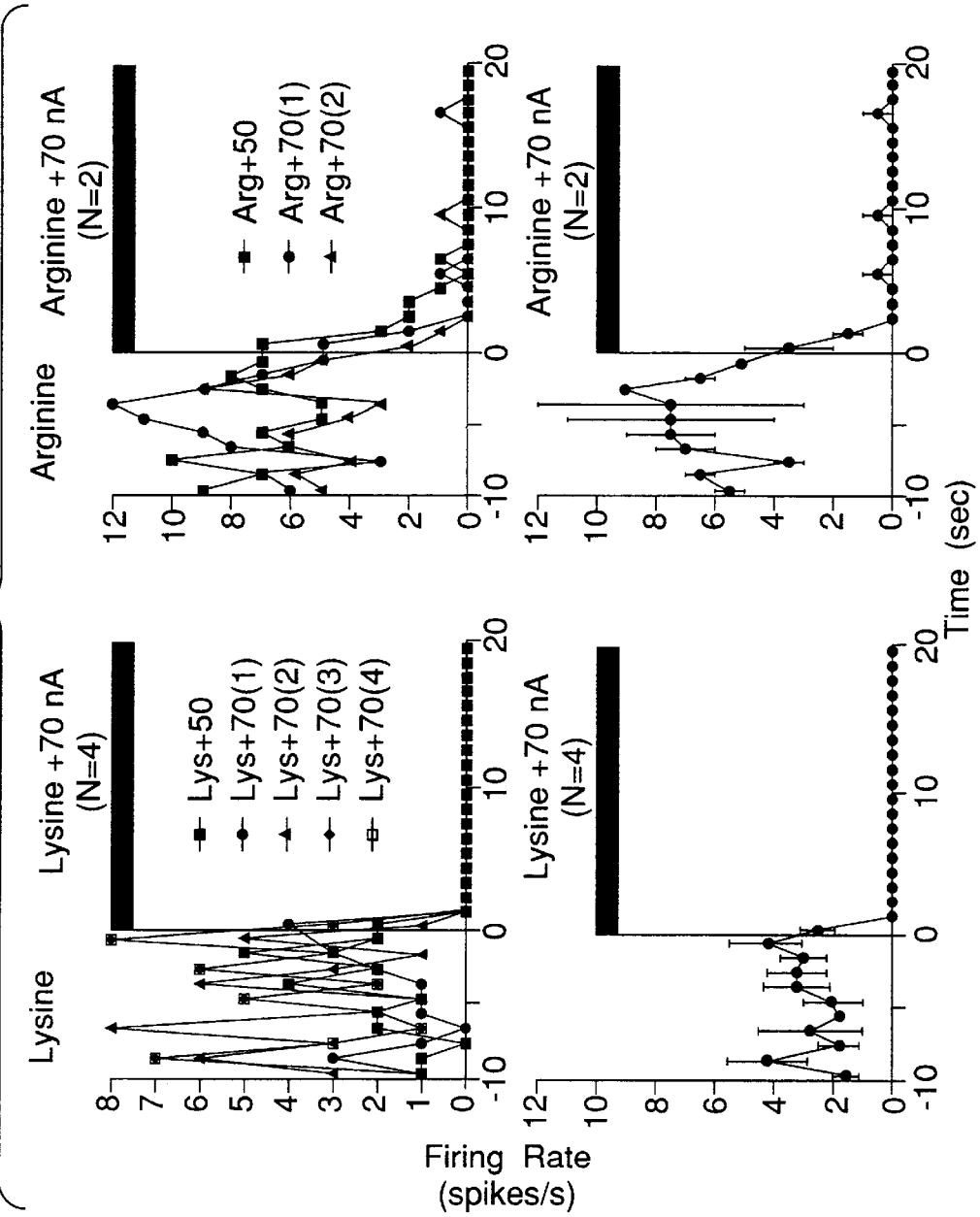
FIG. 3 shows histograms of neuronal activity in the VMH before and after iontophoretic application of lysine (left figures) or arginine (right figures). The upper histograms show neuronal activity of individual neuron and the lower histograms show their mean with ±SEM.

On the other hand, in the neurons which showed glutamic acid-induced activity, remarkable changes were observed by administration of these amino acids, as shown in FIGS. 1–3. FIG. 1 shows an example of single neuronal activity, which shows influences of lysine (Lys), arginine (Arg) and glycine (Gly) on glutamic acid-induced neuronal activity in the VMH. In this example, activity of the neuron was evident during iontophoretic application of glutamic acid from a point denoted by the arrow 'a' (10 nA). The activity of this neuron was not changed by administration of Na$^+$ and Cl$^-$ (70 nA), but it was increased dose-dependently by administration of a large amount of glutamic acid (20 nA, arrow b). This increased activity was then inhibited by the release of lysine in a dose-dependent manner. In particular, the glutamic acid-induced activity was remarkably inhibited for more than 2 minutes by the release of lysine (40 nA), and the inhibited activity was not recovered to the pre-control level.

On the other hand, FIG. 2 shows an example of the single neuronal activity, which shows influences of lysine, arginine and glycine when the basal activity of the VMH neuron was maintained at a higher level by the continuous application of glutamic acid (10 nA). In this neuron, the activity was not changed by the release of glycine. A similar result was obtained when Na$^+$ or Cl$^-$ was released as a control. On the contrary, when lysine and arginine were released, the glutamic acid-induced neuronal activity was inhibited in a dose-dependent manner. Furthermore, glutamic acid (20 nA) was released from a point denoted by the arrow in FIG. 2 to confirm the dose-dependent increase in activity.

FIG. 3 shows histograms of neuronal activity before and after administration of lysine (left figures) and arginine (right figures). The upper histograms show activity of individual neuron and the lower histogram show their mean with ±SEM. FIG. 3 demonstrates that the neuronal activity induced by glutamic acid was inhibited completely within 2–3 seconds after the administration of lysine and arginine.

Accordingly, the present invention can provide a drug inhibiting an excess activity of glutamic acid, an excitatory neurotransmitter, or a drug potentiating a reduced activity of glutamic acid. These drugs can advantageously prevent or relieve diseases such as epilepsy caused by an excess activity of glutamic acid, and such as dementia caused by a reduced activity of glutamic acid.

What is claimed is:

1. A pharmaceutical composition for treatment of memory dysfunction in a patient consisting of a therapeutically effective daily amount in the range from about 1 to 100 grams of L-lysine in a medicament.

2. The composition of claim 1, wherein the medicament is selected for oral administration.

3. The composition of claim 1, wherein the medicament is selected for enteral administration.

4. The composition of claim 1, wherein the medicament is selected for intravenous administration.

5. A method for treating a brain disorder associated with glutamic acid in a subject, comprising administering to the subject, a therapeutically effective amount in the range from about 1 to 100 grams of L-lysine or its resemblance having various protective groups for amino and carboxyl groups, their salts, or condensates, wherein the L-lysine inhibits glutamic acid activity in the brain.

6. The method of claim 5, wherein the disorder is a motor disturbance.

7. The method of claim 6, wherein the motor disturbance is epilepsy.

* * * * *